United States Patent
Schankereli

(10) Patent No.: US 9,211,361 B2
(45) Date of Patent: Dec. 15, 2015

(54) THIN COLLAGEN TISSUE FOR MEDICAL DEVICE APPLICATIONS

(76) Inventor: Kemal Schankereli, Stillwater, MN (US)

(*) Notice: Subject to any disclaimer, the term of this patent is extended or adjusted under 35 U.S.C. 154(b) by 966 days.

(21) Appl. No.: 12/724,311

(22) Filed: Mar. 15, 2010

(65) Prior Publication Data

US 2011/0224779 A1    Sep. 15, 2011

(51) Int. Cl.
*A61F 2/24* (2006.01)
*A61L 27/36* (2006.01)
*A61K 35/34* (2015.01)

(52) U.S. Cl.
CPC ............ *A61L 27/3604* (2013.01); *A61K 35/34* (2013.01); *Y10S 623/922* (2013.01)

(58) Field of Classification Search
CPC ........................................ A61F 2/24
USPC .......................................... 623/2.1
See application file for complete search history.

(56) References Cited

U.S. PATENT DOCUMENTS

| 4,582,640 | A | 4/1986 | Smestad |
| 4,902,289 | A | 2/1990 | Yannas |
| 5,037,377 | A | 8/1991 | Alonso |
| 5,104,405 | A | 4/1992 | Nimni |
| 5,197,977 | A | 3/1993 | Hoffman et al. |
| 2006/0253192 | A1 | 11/2006 | Atala et al. |
| 2007/0162113 | A1* | 7/2007 | Sharkawy et al. ......... 623/2.38 |

FOREIGN PATENT DOCUMENTS

| CN | 200987711 | | 12/2007 |
| EP | 1878407 | A1 | 7/2007 |
| MX | 9504896 | | 5/1997 |
| WO | WO 90/03811 | | 4/1990 |
| WO | WO 99/44533 | | 9/1999 |
| WO | WO 01/91671 | | 12/2001 |
| WO | WO 02/012295 | | 11/2002 |
| WO | WO 03/097809 | | 11/2003 |
| WO | WO 2008/002767 | | 1/2008 |
| WO | WO 2008/101566 | | 1/2008 |

* cited by examiner

*Primary Examiner* — Thomas J Sweet
*Assistant Examiner* — Matthew Schall
(74) *Attorney, Agent, or Firm* — Todd L. Juneau

(57) ABSTRACT

This invention relates to processes of preparing heterogeneous graft material from animal tissue. Specifically, the invention relates to the preparation of animal tissue, in which the tissue is cleaned and chemically cross-linked using both vaporized and liquid cross-linking agents, resulting in improved physical properties such as thin tissue and lowered antigenicity, thereby increasing the ease of delivering the tissue during surgery and decreasing the risk of post-surgical complication, respectively.

17 Claims, 1 Drawing Sheet

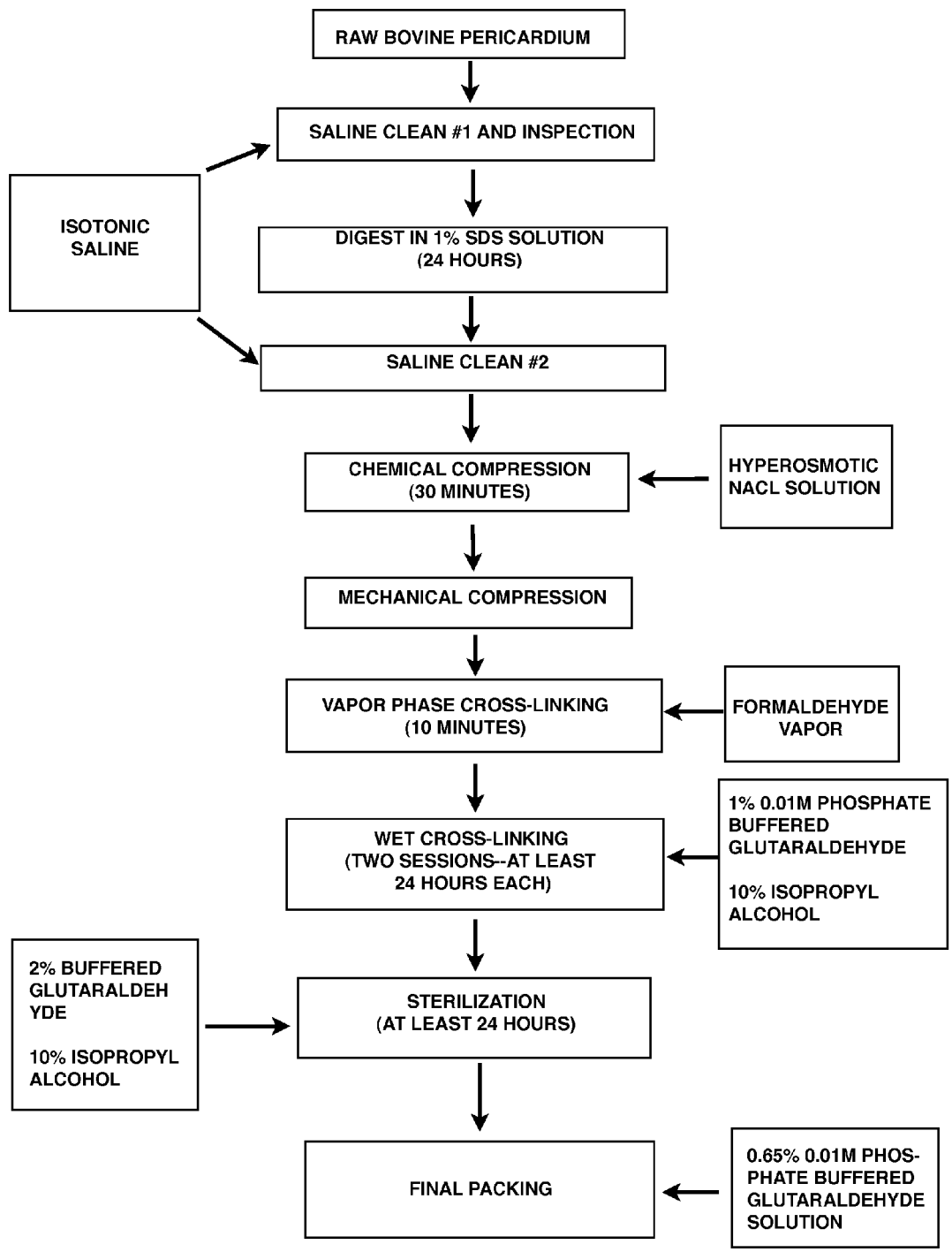

THIN COLLAGEN TISSUE FOR MEDICAL DEVICE APPLICATIONS

CROSS REFERENCE TO RELATED APPLICATIONS n/a

STATEMENT REGARDING FEDERALLY SPONSORED RESEARCH OR DEVELOPMENT

No federal government funds were used in researching or developing this invention.

NAMES OF PARTIES TO A JOINT RESEARCH AGREEMENT n/a

REFERENCE TO A SEQUENCE LISTING n/a.

BACKGROUND

1. Field of the Invention

This invention relates to bioprosthetic transcatheter valve and implant material, processes for preparing bioprosthetic transcatheter valve and implant material from animal tissue, and methods of use thereof. Specifically, the invention relates to the preparation of animal tissue, in which the tissue is cleaned, chemically cross-linked using both vaporized and liquid cross-linking agents, and compressed, resulting in an improved bioprosthetic or implantable material that is substantially non-antigenic, non-thrombogenic, resistant to calcification, durable, and thin enough to be used in applications requiring extremely small valves or implants.

2. Background of the Invention

The use of prepared heterogenous graft material for human surgical implantation is well known. More specifically, the use of treated animal tissue as human tissue grafts, replacement valves, and similar implantation surgical procedures is well known. However, problems of immunogenicity, thrombogenicity, calcification, material strength, and size have not been adequately addressed in the prior art.

Prior to the present invention, animal tissue specimens for surgical use were prepared by first harvesting the selected tissue from beef cattle or other meat supplying animals at the slaughter house. The harvested tissues were then transported to a laboratory where the material was cleaned by mechanically stripping away fat tissue and other undesired components from the harvested specimen material. Next, the cleaned tissue specimen was subjected to a "wet" cross-linking operation in which it is soaked for a predetermined time in a glutaraldehyde solution and finally was dehydrated in an alcohol solution. Subsequently, the sample was thoroughly rinsed to remove traces of the ethyl alcohol and glutaraldehyde and then was packaged in a vial containing a one percent propylene oxide solution as a sterilant.

While the use of cattle or other meat supplying animals ensures an adequate supply of tissue for processing, a combination of (i) the lower natural collagen levels and higher non-collagenous protein levels in the tissue of older animals, (ii) the lack of a processing step to effectively remove non-collagenous proteins, and (iii) the limitations of "wet" cross-linking, when used alone, to bond glutaraldehyde with collagen molecules, results in a product that still exhibits traits of antigenicity, thrombogenicity and calcification that can result in post-surgical complications, as well as limited endothelialization properties.

More specifically, the use of glutaraldehyde alone in chemical cross-linking of tissue results in a tissue sample wherein the release of glutaraldehyde after implantation of the sample results in an increased risk of inflammation in and around the implanted tissue.

For example, U.S. Pat. No. 6,468,313 to Bio-Vascular, Inc. discloses an implant material in the form of a natural animal tissue cross-linked into a pre-formed shape, the tissue being adapted to substantially retain its shape when implanted into a body.

In another example, U.S. Pat. No. 5,507,810 to Osteotech, Inc. discloses fibrous connective tissue for surgical implantation is made substantially antigen-free by contact with one or more extraction agents.

In another example, U.S. Pat. No. 4,681,588 to Ketharanathan discloses material for use in a biological environment is produced by subjecting a sheet of parietal pleura to glutaraldehyde tanning.

In another example, U.S. Pat. No. 4,399,123 to Oliver discloses a fibrous tissue preparation suitable for homo or heterotransplantation obtained by treating mammalian fibrous tissue with a proteolytic enzyme followed, if desired, by further treatment with a carbohydrate splitting enzyme.

However, known procedures for treating animal tissue typically result in tissue thickness too large for surgical use in applications requiring a smaller valve or implant. Tissue samples of this thickness can limit the use of smaller gauge catheters in delivering the tissue sample to the area of the human body in which surgery is to be performed, or limit the types of patients that may be treated to large patients only.

For example, bovine pericardial tissue used in the products Duraguard®, Peri-Guard®, and Vascu-Guard®, all products currently used in surgical procedures, are marketed as being harvested generally from cattle less than 30 months old. However, pericardial tissue from older animals is thicker than younger animals, and thus limits the thinness that can be achieved. Other patents and publications that are directed to the surgical use of harvested, biocompatible animal tissues may disclose thin tissues, however, these tissues are used only as biocompatible "jackets" or sleeves for implantable stents. Accordingly, these tissues do not have the biomechanical, e.g. strength and durability, necessary for the construction of bioprosthetic transcatheter valves, or implants. For example, U.S. Pat. No. 5,554,185 to Block discloses an inflatable prosthetic cardiovascular valve which is constructed so as to be initially deployable in a deflated "collapsed" configuration wherein the valve may be passed through the lumen of a cardiovascular catheter and subsequently inflated to an "operative" configuration so as to perform its intended valving function at its intended site of implantation within the cardiovascular system. In another example, U.S. Pat. No. 7,108,717 to Design & Performance-Cyprus Limited discloses a covered stent assembly comprising a tubular, expandable stent having a metallic framework covered with a cylinder of biocompatible, non-thrombogenic expandable material, such as heterologous tissue. In another example, U.S. Pat. No. 6,440,164 to Scimed Life Systems, Inc. discloses a prosthetic valve for implantation within a fluid conducting lumen within a body includes an elongate generally cylindrical radially collapsible valve body scaffold defining a fluid passageway therethrough for retentive positioning within the lumen. However, these patents describe necessarily elastic materials that are used for covering expandable wire-mesh stents.

Methods do currently exist for production of synthetic bioprosthetic materials in the form of an acellular collagen-based tissue matrix. However, the product suffers from a strength deficiency, is subject to tearing and is not ideal for suture retention. For example, U.S. Pat. No. 5,336,616 to LifeCell Corporation discloses a method for processing and preserving an acellular collagen-based tissue matrix for transplantation. However, to date, the molecular reasons why naturally matured collagen is superior to synthetic have not been fully elucidated.

Accordingly, procedures and devices which address these and other concerns are needed in the field.

BRIEF SUMMARY OF THE INVENTION

In a preferred embodiment, there is provided a process of preparing a bioprosthetic or implant tissue material for use in surgical procedures on humans comprising the steps of: (a) vapor cross-linking a pre-digested compressed tissue specimen by exposing the tissue specimen to a vapor of a cross-linking agent selected from the group consisting of aldehydes, epoxides, isocyanates, carbodiimides, isothiocyanates, glycidalethers, and acyl azides; and (b) chemically cross-linking the vapor-cross-linked tissue specimen by exposing the vapor-crosslinked tissue specimen to an aqueous crosslinking bath for a predetermined time, such crosslinking bath containing a liquid phase of a crosslinking agent selected from the group consisting of aldehydes, epoxides, isocyanates, carbodiimides, isothiocyanates, glycidalethers, and acyl azides.

In a preferred embodiment, there is also provided a tissue material prepared according to the process herein. In another preferred embodiment, the tissue specimen is harvested from a porcine, ovine or bovine animal. Alternatively, the predetermined tissue specimen is taken from a bovine animal 30 days old or less. In one preferred embodiment, the tissue specimen is taken from an animal that is not more than about 10 days old, and in a preferred embodiment about 5 days old.

In another preferred embodiment the harvested tissue specimen comprises a collagen-based tissue selected from the group consisting of pericardium, dura mater, heart valves, blood vessels, fascia, ligaments, tendons, and pleura tissue.

In preferred processes, the tissue specimen is subjected to chemical dehydration/compression and mechanical compression before cross-linking, and/or the pre-digested tissue specimen is provided by digesting a harvested, cleaned pericardial tissue in a solution containing a surfactant. In a preferred embodiment, the surfactant is 1% sodium laurel sulfate.

Preferably, the chemical dehydration/compression comprises subjecting the tissue specimen to hyperosmotic salt solution.

The mechanical compression may preferably comprise subjecting the tissue specimen to a roller apparatus capable of compressing the tissue specimen to a thickness ranging from about 0.003' (0.0762 mm) to about 0.010" (0.254 mm).

In another preferred embodiment, there is provided a process of preparing animal-derived collagen tissue material for use in surgical procedures on humans comprising the steps of: (a) vapor cross-linking a pre-digested collagen tissue specimen by exposing the tissue specimen to a formaldehyde vapor phase; and (b) subjecting the vapor-crosslinked collagen tissue specimen to an aqueous glutaraldehyde bath for a predetermined time.

Also contemplated is a tissue for bioprosthetic or implant use in the human body prepared according to the process herein.

In another preferred embodiment, there is provided a process of preparing a bioprosthetic transcatheter valve material for use in surgical procedures on humans comprising the steps of: (a) vapor cross-linking a pre-digested compressed bovine pericardium tissue specimen by exposing the tissue specimen to a formaldehyde vapor phase; and (b) subjecting the vapor-crosslinked tissue specimen to an aqueous glutaraldehyde bath for a predetermined time.

In another preferred embodiment, it is contemplated to include a step of sterilizing the cross-linked tissue specimen.

In another preferred embodiment, it is contemplated to further comprise wherein the compression of the tissue specimen is subjecting to chemical dehydration/compression and mechanical compression.

In another preferred embodiment, it is contemplated to further comprise wherein the pre-digested tissue specimen is provided by digesting a harvested, cleaned bovine pericardial tissue in a solution containing a surfactant. Preferably, the surfactant is 1% sodium laurel sulfate.

In another preferred embodiment, it is contemplated to further comprise wherein the chemical dehydration/compression comprises subjecting the tissue specimen to hyperosmotic salt solution and wherein the mechanical compression comprises subjecting the tissue specimen to a roller apparatus capable of compressing the tissue specimen to a thickness ranging from about 0.003' (0.0762 mm) to about 0.010" (0.254 mm).

In another preferred embodiment, there is provided a bioprosthetic transcatheter valve material for use in the human body prepared according to the processes herein.

In yet another preferred embodiment, there is provided a process of preparing heterogenous or homogenous tissue material for use in surgical procedures on humans wherein an animal collagen tissue specimen is chemically cross-linked first by exposing the tissue to formaldehyde vapor for approximately 10 minutes, and second by immersing the tissue in a glutaraldehyde solution for two consecutive sessions of approximately 24 hours each.

In another preferred embodiment, there is provided a process of converting pericardial tissue specimen taken from a bovine animal not more than 30 days old to a non-antigenic, non-thrombogenic, calcification-resistant implantable material for use in surgical procedures on humans wherein the pericardial tissue specimen is cleaned, digested by surfactant, compressed to approximately 0.003" in thickness, vapor cross-linked by exposing the tissue to a vapor-phase cross-linking agent selected from the group consisting of aldehydes, epoxides, isocyanates, carbodiimides, isothiocyanates, glycidalethers, and acyl azides, and liquid-phase cross-linked by immersing the tissue in a liquid cross-linking agent selected from the group consisting of aldehydes, epoxides, isocyanates, carbodiimides, isothiocyanates, glycidalethers, and acyl azides.

In another preferred embodiment, it is contemplated to provide an implantable tissue material prepared according to the processes herein.

In another preferred embodiment, there is provided a process of converting pericardial tissue specimen taken from a bovine animal not more than 30 days old to a non-antigenic, non-thrombogenic, calcification-resistant implantable material for use in surgical procedures on humans wherein the pericardial tissue specimen is cleaned, digested by surfactant, compressed to approximately 0.003" in thickness, vapor cross-linked by exposing the tissue to formaldehyde vapor for approximately 10 minutes, and further cross-linked by immersing in a glutaraldehyde solution for at least 24 hours.

In another preferred embodiment, it is contemplated to provide a bioprosthetic or implantable material prepared according to the process herein.

Also contemplated is a tissue material as claimed herein, in dehydrated state for dry packaging.

In another preferred embodiment, it is contemplated to provide a tissue material as claimed for use wherein such material is trimmed and/or configured to an appropriate shape as replacement tissue for any of the following surgical purposes: stented or stentless pericardial valve replacement, stented or stentless pulmonic valve replacement, transcatheter valvulare prosthesis, aortic bioprosthesis/valve replacement or repair, annuloplasty rings, bariatric surgery, dural patching, enucleation wraps, gastric banding, herniation repair, lung surgery e.g. lung volume reduction, peripheral arterial or venous valve replacement, pericardial patching, rotator cuff repair, urethereal slings, valve repair, vascular patching, valve conduit insertion, or arterial conduit insertion.

Preferably, the tissue material as claimed in any of claims comprises a very thin, durable material that ranges from about 0.002" (0.0508 mm) to about 0.020" (0.508 mm) as the average cross-sectional thickness. At the lower end of this range, the focus is on being able to create materials, tissues, and devices that can access applications where a very thin, very durable material is needed. At the upper range of the present invention, the focus may not necessarily be on the thinness of the material compared to the 0.002" (0.0508 mm) materials; however, the durability, and the ability to form materials, tissues and devices from a wider range of starting materials and sources. In another preferred embodiment, the present invention ranges from about 0.002" (0.0508 mm) and about 0.010" (0.254 mm) in thickness. In another preferred embodiment, the present invention ranges from about 0.002" (0.0508 mm) and about 0.005" (0.127 mm) in thickness. In one preferred embodiment, the present invention averages approximately 0.003" (0.0762 mm) in thickness.

In another preferred embodiment, it is contemplated to provide a tissue material as claimed wherein the tissue material is provided in sterile form and is adapted to be implanted into a body and attached in place. For example, the material may be configured in a spherical form to wrap an orbital implant, or configured to form leaflets in a prosthetic transcatheter valve.

In another preferred embodiment, it is contemplated to provide a stent assembly for maintaining the patency of a body lumen comprising an expandable stent with or without a biocompatible jacket, and a prosthetic transcatheter valve made from the inventive tissue material disposed therein to function as a valve replacement.

It is also contemplated to manufacture a prosthetic transcatheter valve made from the tissue material configured for delivery within an intravenous catheter measuring 18 or less in french gauge, or even within a gauge 14 or less french gauge.

In a preferred embodiment, a process of preparing animal tissue for use in surgical procedures on humans comprising the steps of:

harvesting a predetermined tissue specimen from a bovine animal at the time of slaughter of such animal;

cleaning the tissue specimen a first time to remove unwanted components;

digesting the tissue to denucleate and to remove non-collagenous proteins;

cleaning the tissue specimen a second time to remove unwanted components;

chemically compressing the tissue specimen, including with a hyperosmotic solution;

mechanically compressing the tissue specimen;

chemically cross-linking the compressed tissue specimen by exposing the tissue to a vapor selected from the group consisting of aldehydes, epoxides, isocyanates, carbodiimides, isothiocyanates, glycidalethers, and acyl azides, but especially formaldehyde;

chemically cross-linking the compressed tissue specimen by exposing the tissue to an aqueous bath for a predetermined time, such bath containing a solute selected from the group consisting of aldehydes, epoxides, isocyanates, carbodiimides, isothiocyanates, glycidalethers, and acyl azides, but especially glutaraldehyde;

sterilizing the tissue specimen, for example, by exposing the tissue to an ethanol soak for a predetermined time; and optionally placing the sterilized tissue specimen in a sterilized package.

Preferred embodiments include, wherein the harvested tissue specimen comprises a collagen-based tissue selected from the group consisting of pericardium, dura mater, heart valves, blood vessels, fascia, ligaments, tendons, and pleura tissue.

Methods of use include using the tissue configured to an appropriate shape as replacement tissue for any of the following surgical purposes: stented or stentless pericardial valve replacement, stented or stentless pulmonic valve replacement, transcatheter valvulare prosthesis, aortic bioprosthesis/valve replacement or repair, annuloplasty rings, bariatric surgery, dural patching, enucleation wraps, gastric banding, herniation repair, lung surgery e.g. lung volume reduction, peripheral arterial or venous valve replacement, pericardial patching, rotator cuff repair, urethereal slings, valve repair, vascular patching, valve conduit insertion, or arterial conduit insertion.

BRIEF DESCRIPTION OF THE DRAWINGS

FIG. 1 is a flow chart evidencing the steps of the process claimed herein.

DETAILED DESCRIPTION OF THE INVENTION

Definitions

The following definitions are provided as an aid to understanding the detailed description of the present invention.

"Bobby calf" as used herein means a male or a female calf of a dairy cow that is slaughtered before weaning, usually not more than 30 days from birth.

"Collagen" is the most abundant protein in all animal tissue, and is the primary component of connective tissue. Collagen consists of a protein with three polypeptide chains, each containing approximately 1000 amino acids and having at least one strand of repeating amino acide sequence Gly-X-Y, where X and Y can be any amino acid but usually are proline and hydroxyproline, respectively. Collagen assembles into different supramolecular structures and has exceptional functional diversity.

Natural collagen sources contemplated as within the scope of the present invention include porcine, ovine, or bovine animals 30 days old or less. In one preferred embodiment, the tissue specimen is taken from an porcine, ovine, or bovine animal that is not more than about 10 days old, and in a preferred embodiment about 5 days old. Preferred embodiments include specific tissues, wherein the harvested tissue specimen comprises a collagen-based tissue selected from the group consisting of pericardium, dura mater, heart valves, blood vessels, fascia, ligaments, tendons, and pleura tissue.

"Cross-links" are bonds that link one polymer chain to another. They can be covalent bonds or ionic bonds. "Polymer chains" can refer to synthetic polymers or natural polymers, including proteins such as collagen. Examples of some common crosslinkers are the dimethyl suberimidate, formaldehyde and glutaraldehyde. Each of these crosslinkers induces nucleophilic attack of the amino group of lysine and subsequent covalent bonding via the crosslinker.

"Pyridyl" encompasses a set of functional groups in the pyridine derivative chemical class with the common structure $C_5N_1$. A pyridyl group will bond an aldehyde compound to a collagen protein through the cross-linking process.

"Surfactants" are wetting agents that lower the surface tension of a liquid, allowing easier spreading, and lower the interfacial tension between two liquids. The term surfactant is a blend of "surface active agent". Surfactants are usuallyorganic compounds that are amphiphilic, meaning they contain both hydrophobic groups (their "tails") and hydrophilic groups (their "heads"). Therefore, they are soluble in both organic solvents and water. Surfactants are also often classified into four primary groups: anionic, cationic, non-ionic, and zwitterionic (dual charge). A non-limiting preferred surfactant contemplated herein is sodium laurel sulfate, although various other surfactants known to a person of ordinary skill in the art are also contemplated as within the scope of the invention.

The use of Bobby calf (BC) pericardial tissue for prostheses provides a number of benefits over alternative tissue sources. BC animals are primarily used for the production of veal, meaning that a large and steady supply of tissue from such animals is available. BC pericardial tissue is known to be extremely thin, typically in the range of 0.005" to 0.007" (0.1270 mm to 0.1778 mm). Pericardial tissue from such animals also has a very high natural collagen content, providing the tissue both high strength and a variety of biocompatibility benefits, including low antigenicity, thrombogenicity and calcification potential; high endothelialization; high suture retention; and high bursting strengths. As the animal ages, the natural collagen content of its tissue decreases, and these biocompatibility benefits also decrease.

Increasing the collagen content of a given specimen of animal tissue, and simultaneously decreasing the presence of non-collagenous proteins in such tissue results in a heightened biocompatibility of treated tissue samples. The high natural collagen content of BC pericardial tissue makes it an excellent source of tissue for collagen-enhancing treatment.

Treatment of BC pericardial tissue for use in surgical transplantation should begin with an isotonic saline wash at room temperature, whereupon the sample should be split to form a flat sheet and then returned to the saline solution to await further processing. Formation of a flat sheet of tissue allows for later trimming and manipulation to form shapes specifically tailored to individual surgeries.

Washing a tissue sample with a surfactant/water solution for a period of up to 24 hours can result in a 99:1 post-treatment ratio of collagen to non-collagenous proteins in the tissue. Such a high ratio greatly enhances the effectiveness of later collagen cross-linking to further improve biocompatibility of the sample.

Thinness of tissue used for surgical implants and grafts provides many benefits in surgery. The thickness of such material directly affects the size of any product or device made with such a material, for example a heart valve, arterial valve, or venous valve. Further, the smaller size impacts the ease with which the material may be introduced into the human body, through catheterization or otherwise, as well as the ease of manipulation of the material after placement. A thinner sample means a lower gauge catheter, and easier intravenous or percutaneous insertion, and thus the ability to treat a higher percentage of the patient population requiring such an intervention.

BC pericardial tissue that has been surfactant treated and attained a very high collagen content becomes ideally suited to compression to further thin the tissue sample. BC pericardial tissue of the present invention may be about at least 95% to about at least 99% collagen. In a non-limiting preferred embodiment, the collagen content is about 99%. Suspension in a hyperosmotic solution for a period of 30 minutes will substantially thin the tissue through partial dehydration.

Collagen-enhanced and partially dehydrated BC pericardial tissue may be further thinned by means of mechanical compression, and the high bursting strength of such tissue will prevent tearing or weakening of the tissue in the process. A preferred method of mechanically compressing a tissue sample is to place it between two sheets of polyethylene film, each larger in surface area than the tissue sample, and covering the entire upper and lower surfaces of the tissue sample, and placing the sample and film into one of (i) a wringer apparatus comprising upper and lower electrically or manually driven rollers, with the gap between such rollers set at approximately 0.002" to 0.020" using a feeler gauge, wherein the tissue sample and film are fed through the apparatus, or (ii) a press apparatus comprising upper and lower plates, wherein the plates are compressed via manual or electrically driven turning mechanism until reaching a gap set at approximately 0.002" to 0.020" using a feeler gauge, wherein the tissue sample and film are fed through the apparatus. Additional preferred methods of mechanical compression of a tissue sample include subjecting the sample to a vacuum compression, or applying weighted or compressive force to the sample.

BC pericardial tissue subjected to dehydration compression and mechanical compression as detailed herein is known to attain a tissue thickness of approximately 0.003" (0.0762 mm), making BC tissue at least 40% thinner than bovine tissue currently in use on the surgical market, without compromising the strength of the tissue, and therefore is highly desirable as a material for surgical implants and grafts. It is contemplated as within the scope of the invention that tissue thicknesses of about 0.002" (0.0508 mm) to about 0.007" (0.1778 mm), without limitation, may be manufactured according to the inventive process.

Once subjected to compression treatment, the BC pericardial tissue is ready for collagen cross-linking Cross-linking is a process well known in the art for improving the biocompatibility of collagen in a piece of tissue prior to surgical implantation. Processes for collagen cross-linking currently known in the art have been limited to the "tanning", or submersion of a tissue sample in a wet bath containing a cross-linking agent, such as an aldehyde, as a solute.

An ideal primary method for cross-linking collagen in tissue comprises placing such tissue onto a pin frame such that the edges are held firmly in place. The frame and tissue sample are then placed into a chamber equipped with each of an inlet and outlet port for submission to a "vapor cross-linking" process. The inlet port is attached to a stoppered flask comprising each of an inlet and outlet port and containing a bolus of polyoxymethylene, which flask is gently heated as air flow is simultaneously initiated from the flask into the chamber containing the tissue sample, thereby producing formaldehyde vapors which flood the chamber for a period of 10 minutes, after which time such vapors are evacuated from the chamber and the pin frame and tissue sample are removed intact therefrom.

The use of heated polyoxymethylene to create formaldehyde vapor is superior to the known method of heating liquid glutaraldehyde, as the latter decreases the efficiency of the vapor delivery mechanism by releasing water vapor. Water vapor will swell the tissue material, whereas the use of a formaldehyde vapor results in a relatively anhydrous cross-linking process. By not allowing excess water during this phase of the process, the tissue material maintains its thin profile. However, gas cross-linking with formaldehyde is limited by the structural size of formaldehyde and the available of a single aldehyde group.

After completion of the vapor cross-linking, the tissue material is subjected to a liquid glutaraldehyde bath. Glutaraldehyde provides a further cross-linking that results in additional cross-links that formaldehyde cannot achieve. The presence of two aldehyde groups for cross-linking and the ability to be cross link over a distance since glutaraldehyde has a three-carbon chain connecting the two carbonyl moieties further strengthens the tissue material. In one non-limiting preferred embodiment, the pin frame and tissue sample are then transferred into an aqueous bath containing 1% 0.01M phosphate buffered glutaraldehyde and 10% isopropyl alcohol at a temperature of approximately 40 degrees C., and gently stirred for a period of not less than 24 hours, although variations of glutaraldehyde cross-linking are well known in the art and are considered within the scope of this step of the present invention.

Although the combination of vapor formaldehyde cross-linking with wet glutaraldehyde cross-linking results in improved stability of the cross-links when compared to a sample subjected to the latter process alone, the combination of formaldehyde vapor and glutaraldehyde liquid appears to provide an additional benefit to the material that results from the inventive process. The bioprosthetic or implant material of the present invention does not exhibit the immunogenic problems known in the art that accompanies glutaraldehyde cross-linked materials. Prior research has shown that glutaraldehyde can trigger a strong inflammatory reaction within a mammalian body, even including anaphylactic reactions. However, the material produced by the present inventive process is non-antigenic.

It is believed that the use of glutaraldehyde alone in chemical cross-linking of tissue is known to create cross-linking that is susceptible to opening and releasing glutaraldehyde after implantation of the sample. The result of such degradation of the cross-links is an increased risk of inflammation in and around the implanted tissue. In contrast, when pre-treating the sample with vapor formaldehyde via the method described herein, the formaldehyde acts as a reducing agent, creating cyclic pyridine molecules. The process of creating stable, non-reactive aromatics on the exposed surface of the collagen is believed to progress by nucleophilic attack by formaldehyde on the carbonyl of the glutaraldehyde-linked amine of the lysine, histidine, and/or arginine, improving the stability of the molecular structure of the sample and reducing the antigenicity of the sample compared to a sample treated with glutaraldehyde alone. A redcued inflammatory response and lower degree of capsule formation provides a distinct advantage.

After the completion of wet cross-linking, the tissue sample, still attached to the pin frame, is sterilized by transferring it to an aqueous bath consisting essentially of a 2% buffered glutaraldehyde solution containing 10% isopropyl alcohol, and is soaked therein at 42 degrees C. for a period of no less than 24 hours. Upon completion of sterilization, the tissue sample is removed from the pin frame.

Finally, the tissue sample is packaged for transport in a container together with a sterilizing 0.65%, 0.01M phosphate buffered glutaraldehyde solution, in which solution the tissue sample may either float freely or be held stationary by attachment to a mylar film.

Upon removal from packaging, the tissue sample may be trimmed, sutured or otherwise manipulated to form the size and shape necessary for any implantation surgery for which such tissue would be appropriate.

For example, in one preferred embodiment, the tissue would be trimmed to fit for any necessary vascular or pericardial patching. In another preferred embodiment, the tissue would be sutured to form a cylinder to cover a mesh stent. In another embodiment, the tissue would be cut into a leaflet shape for prosthetic transplantation into a mitral valve. In yet another preferred embodiment, a strip of tissue would be cut and sutured into an annular shape for transplantation into a mitral valve.

Methods of use include using the tissue configured to an appropriate shape as replacement tissue for any of the following surgical purposes: stented or stentless pericardial valve replacement, stented or stentless pulmonic valve replacement, transcatheter valvulare prosthesis, aortic bioprosthesis/valve replacement, annuloplasty rings, bariatric surgery, dural patching, enucleation wraps, gastric banding, herniation repair, lung surgery e.g. lung volume reduction, peripheral arterial or venous valve replacement, pericardial patching, rotator cuff repair, uretheral slings, valve repair, vascular patching, valve conduit insertion, or arterial conduit insertion.

Referring now to the FIGURES:

FIG. 1 shows a flow chart evidencing the steps and materials used in the BC pericardial tissue treatment process.

Example 1

In this example, the pericardial sac from a bobby calf is washed with isotonic saline at room temperature, held in saline for processing, then inspected for acceptability and split into a flat sheet approximately 7×9 cm in dimension. The washed sample is then subjected to "digestion", in which a detergent extraction to de-nucleate the tissue and remove non-collagenous proteins, preferably using a 1% sodium lauryl sulfate solution (SDS). The sample is held in this solution and gently stirred for up to 24 hours. Histological review of the tissue will indicate that the tissue has been de-nucleated and that non-collagenous proteins have been almost entirely removed. Gross observation of the tissue will indicate a color change from the original tan/white color to pure white. Digestion has the side effect of swelling the tissue.

Following digestion, the swollen tissue is washed again in isotonic saline until the SDS is removed. This process also reverses some of the swelling from digestion. Next, the tissue is further "chemically compressed" by dehydration by placing it in a hyperosmotic NaCl solution for a period of 30 minutes, during which time the sample is gently stirred. Upon removal, the sample is placed between two sheets of polyethylene film and subjected to mechanical compression, either using mechanical rollers, a press, or similar mechanism, resulting in a flattened sample approximately 0.003" in thickness. The polymer films are then removed and the sample is momentarily held on a dry surface.

Next, the compressed tissue is subjected to an initial cross-linking phase, in which the tissue is first placed onto a pin frame with all edges of the tissue held in place. The tissue/ frame is then placed into a box or similar chamber with an outlet port, and an inlet port. The inlet port is attached via a tube to an outlet port emanating from an Erlenmeyer flask, which flask is also equipped with a stopper and an inlet port, and contains a bolus of polyoxymethylene. The flask is gently heated, drawing air from the inlet port, releasing the cross-linking agent formaldehyde vapor, and pushing the vapor out the outlet port and into the chamber containing the tissue sample. The chamber is flooded with vapor for approximately 10 minutes, after which the chamber is evacuated of vapor and the tissue/frame is removed.

The tissue/frame is then transferred to an aqueous bath containing 1%, 0.01M phosphate buffered glutaraldehyde and 10% isopropyl alcohol for a second phase of cross-linking The glutaraldehyde solution will have been prepared according to the teaching of U.S. Pat. No. 7,303,757. The bath will be maintained at approximately 40 degrees C., and the submerged tissue will be gently stirred therein for no less than 24 hours. At such time, the bath solution will be discarded and replaced, and gentle stirring will resume for a second period of no less than 24 hours.

Upon completion of the second cross-linking phase, the tissue is removed from the pin frame and sterilized by immersion for a minimum of 24 hours in a 2% buffered glutaraldehyde solution containing 10% isopropyl alcohol, maintained at approximately 42 degrees C. Upon removal from this solution, the sterile tissue is packed for shipment into a 0.65%, 0.01M phosphate buffered glutaraldehyde solution, in which the sample may either float freely, or be attached to a mylar film and held stationary within the container.

Example 2

In this example, pericardial tissue, valve tissue or tendon tissue from one of a bovine, porcine or ovine animal is washed with isotonic saline at room temperature, held in saline for processing, then inspected for acceptability and split into a flat sheet. The washed sample is then subjected to "digestion", in which a detergent extraction to de-nucleate the tissue and remove non-collagenous proteins, preferably using a solution in which the solute is sodium lauryl sulfate (SDS) or another surfactant. The sample is held in this solution and gently stirred for more than 24 hours. Gross observation of the tissue will indicate a color change from the original tan/white color to pure white, at which time the digestion process will be discontinued. Histological review of the tissue will indicate that the tissue has been de-nucleated and that non-collagenous proteins have been largely removed. Digestion has the side effect of swelling the tissue.

Following digestion, the swollen tissue is washed again in isotonic saline until the surfactant is removed. This process also reverses some of the swelling from digestion. Next, the tissue is further "chemically compressed" by dehydration by placing it in a hyperosmotic solution for a period of 30 minutes, during which time the sample is gently stirred. Upon removal, the sample is placed between two sheets of polyethylene film and subjected to mechanical compression, either using rollers, weights, a press, a vacuum or or similar mechanism, resulting in a flattened sample between about 0.003" (0.0762 mm) and about 0.007" (0.1778 mm) in thickness. The polymer films are then removed and the sample is momentarily held on a dry surface.

Next, the compressed tissue is subjected to an initial cross-linking phase, in which the tissue is first placed onto a pin frame with all edges of the tissue held in place. The tissue/frame is then placed into a box or similar chamber with an outlet port, and an inlet port. The inlet port is attached via a tube to an outlet port emanating from an Erlenmeyer flask, which flask is also equipped with a stopper and an inlet port, and contains a bolus of polyoxymethylene. The flask is gently heated, drawing air from the inlet port, releasing the cross-linking agent formaldehyde vapor, and pushing the vapor out the outlet port and into the chamber containing the tissue sample. The chamber is flooded with vapor for approximately 10 minutes, after which the chamber is evacuated of vapor and the tissue/frame is removed.

The tissue/frame is then transferred to an aqueous bath containing between 0.1%-5.0%, 0.01M phosphate buffered glutaraldehyde and 10% isopropyl alcohol for a second phase of cross-linking. The glutaraldehyde solution will have been prepared according to the teaching of U.S. Pat. No. 7,303,757, or any functionally similar method known to persons of ordinary skill in the art. The bath will be maintained at approximately 40 degrees C., and the submerged tissue will be gently stirred therein for no less than 24 hours. At such time, the bath solution will be discarded and replaced, and gentle stirring will resume for a second period of no less than 24 hours.

Upon completion of the second cross-linking phase, the tissue is removed from the pin frame and sterilized by immersion for a minimum of 24 hours in a solution containing between 1%-5% buffered glutaraldehyde and 10% isopropyl alcohol, maintained at approximately 42 degrees C. Upon removal from this solution, the sterile tissue is packed for shipment into a 0.65%, 0.01M phosphate buffered glutaraldehyde solution, in which the sample may either float freely, or be attached to a mylar film and held stationary within the container.

The references recited herein are incorporated herein in their entirety, particularly as they relate to teaching the level of ordinary skill in this art and for any disclosure necessary for the commoner understanding of the subject matter of the claimed invention. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

What is claimed is:

1. A prosthetic tissue material for surgical purposes which is substantially non-antigenic, non-thrombogenic, calcification-resistant, and tear-resistant comprising a vapor-crosslinked and liquid-crosslinked collagen material comprised of 95-99% collagen that is derived from denucleated, digested, and compressed collagen-based tissue, said prosthetic tissue material having an average cross-sectional thickness ranging from 0.0508 mm to 0.508 mm.

2. The prosthetic tissue material according to claim 1, wherein the tissue material is in dehydrated state for dry packaging.

3. The prosthetic tissue material according to claim 1, wherein the tissue material is trimmed and/or configured to an appropriate shape as a prosthetic tissue selected from the group consisting of: a stented or stentless pericardial valve replacement, a stented or stentless pulmonic valve replacement, a transcatheter valve prosthesis, an aortic bioprosthesis/valve replacement or repair, an annuloplasty ring, a prosthesis for bariatric surgery, a dural patch, an enucleation wrap, a gastric band, a prosthesis for herniation repair, a prosthesis for lung surgery e.g. lung volume reduction, a peripheral arterial or venous valve replacement, a pericardial patch, a prosthesis for rotator cuff repair, a urethral sling, a prosthesis for valve repair, a vascular patch, a valve conduit insertion, and an arterial conduit insertion.

4. The prosthetic tissue material according to claim 1, wherein the tissue material is between about 0.002" (0.0508 mm) and about 0.005" (0.127 mm) in thickness.

5. The prosthetic tissue material according to claim 1, wherein the tissue material is approximately 0.003" (0.0762 mm) in thickness.

6. The prosthetic tissue material according to claim 1, wherein the tissue material is provided in sterile packaging.

7. The prosthetic tissue material according to claim 1, wherein the tissue material is configured in a spherical form to wrap an orbital implant.

8. The prosthetic tissue material according to claim 1, wherein the tissue material is configured to form leaflets in a prosthetic transcatheter valve.

9. The prosthetic tissue material according to claim 1, wherein the tissue material is configured as a valve replacement in an expandable stent assembly for maintaining the patency of a body lumen.

10. The prosthetic tissue material according to claim 1, wherein the tissue material is configured as a biocompatible jacket for an expandable prosthetic stent.

11. The prosthetic tissue material according to claim 1, wherein the prosthetic tissue material is vapor-crosslinked using a vapor-phase cross-linking agent selected from the group consisting of aldehydes, epoxides, isocyanates, carbodiimides, isothiocyanates, glycidalethers, and acyl azides.

12. The prosthetic tissue material according to claim 1, wherein the prosthetic tissue material is vapor-crosslinked using vapor-phase formaldehyde.

13. The prosthetic tissue material according to claim 1, wherein the prosthetic tissue material is liquid-crosslinked using a liquid-phase cross-linking agent selected from the group consisting of aldehydes, epoxides, isocyanates, carbodiimides, isothiocyanates, glycidalethers, and acyl azides.

14. The prosthetic tissue material according to claim 1, wherein the prosthetic tissue material is liquid-crosslinked using aqueous glutaraldehyde.

15. The prosthetic tissue material according to claim 1, wherein the collagen-based tissue is selected from the group consisting of pericardium, dura matter, heart valves, blood vessels, fascia, ligament, tendon, and pleura tissue.

16. The prosthetic tissue material according to claim 1, wherein the collagen-based tissue is selected from the group consisting of bovine pericardium, porcine pericardium, and ovine pericardium.

17. The prosthetic tissue material according to claim 1, wherein the collagen material is comprised of about 99% collagen content.

* * * * *

UNITED STATES PATENT AND TRADEMARK OFFICE
CERTIFICATE OF CORRECTION

PATENT NO.       : 9,211,361 B2  
APPLICATION NO.  : 12/724311  
DATED            : December 15, 2015  
INVENTOR(S)      : Schankereli Page 1 of 1

It is certified that error appears in the above-identified patent and that said Letters Patent is hereby corrected as shown below:

on the title page please change item 76 to item 75 please add item (73) ASSIGNEE AS CORRECTED

PERIDYNE MEDICAL, LLC

Signed and Sealed this  
First Day of March, 2016

Michelle K. Lee  
*Director of the United States Patent and Trademark Office*